(12) United States Patent
Lincoln et al.

(10) Patent No.: US 7,585,466 B1
(45) Date of Patent: Sep. 8, 2009

(54) AUTOMATIC GENOTYPE DETERMINATION

(75) Inventors: Stephen E. Lincoln, Cockeysville, MD (US); Michael R. Knapp, Baltimore, MD (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/618,178

(22) Filed: Jul. 18, 2000

Related U.S. Application Data

(63) Continuation of application No. 09/088,820, filed on Jun. 2, 1998, now abandoned, which is a continuation of application No. 08/362,266, filed on Dec. 22, 1994, now Pat. No. 5,762,876, which is a continuation-in-part of application No. 08/173,173, filed on Dec. 23, 1993, now abandoned.

(51) Int. Cl.
*G01N 21/25* (2006.01)
*G01N 21/29* (2006.01)

(52) U.S. Cl. ............................ 422/82.08; 422/67; 435/6

(58) Field of Classification Search .................... 435/6, 435/91.1, 91.2; 536/23.1, 243; 702/19, 20
See application file for complete search history.

(56) References Cited

U.S. PATENT DOCUMENTS

| | | | |
|---|---|---|---|
| 4,309,112 A | 1/1982 | Ashley et al. | |
| 4,852,017 A | 7/1989 | Hunkapiller | |
| 5,221,518 A | 6/1993 | Mills | |
| 5,415,839 A | 5/1995 | Zaun et al. | |
| 5,443,791 A | 8/1995 | Cathcort et al. | |
| 5,449,621 A | 9/1995 | Klein | |
| 5,453,247 A | 9/1995 | Beavis et al. | |
| 5,516,663 A * | 5/1996 | Backman et al. | ........... 435/91.2 |
| 5,700,637 A | 12/1997 | Southern | |
| 5,811,235 A | 9/1998 | Jeffreys | |
| 5,853,989 A | 12/1998 | Jeffreys et al. | |

FOREIGN PATENT DOCUMENTS

| | | | |
|---|---|---|---|
| AU | 03355093 A1 | | 6/1993 |
| WO | 8803957 | | 6/1988 |
| WO | 9004651 | | 5/1990 |
| WO | 9215712 | | 9/1992 |
| WO | WO 92/15712 | * | 9/1992 |
| WO | 9311262 | | 6/1993 |

OTHER PUBLICATIONS

Kimpton et al, "Automated DNA profiling employing multiplex amplification of short tandem repeat loci", PCR Meth. Appl. 3:13-22. (Aug. 1993).*

(Continued)

*Primary Examiner*—Teresa E Strzelecka
*Assistant Examiner*—Stephanie K Mummert
(74) *Attorney, Agent, or Firm*—Kalow & Springut LLP; Scott D. Locke, Esq.

(57) ABSTRACT

Genotypes of a subject may be determined by analyzing a biological sample. Measurements of the intensity of allele specific signals may be obtained and used to generate reaction values. These reaction values may be compared to probability distributions in order to obtain conditional probabilities of genotypes of interest. The genotype of the subject may be determined based on the measures of these conditional probabilities.

27 Claims, 6 Drawing Sheets

OTHER PUBLICATIONS

Clark, Andrew, "Inference of haplotypes from PCR amplified samples of diploid populations", Mol. Biol. Evol. 7(2):111-122, (Mar. 1990).*

Ledwina et al, "Testing for Hardy-Weinberg Equilibrium", Biometrics (1980) 36:161-165.*

JeanPierre, "Hazard and probabilities of unknown genotypes", Ann. Hum. Genet. (1992) 56:325-330.*

Kimpton et al "Automated DNA Profiling Employing Multiplex Amplification of Short Tandem Repeat Loci", PCR Meth. Appl. (Aug. 1993) 3:13-22).*

Ott et al. (PNAS, 1989, vol. 86, p. 4175-4178).*

O'Connell et al. (Am. J. Hum. Genet., 1998, vol. 63, p. 259-266).*

Nikiforov et al. (Nucleic Acids Research, 1994, vol. 22, No. 20, p. 4167-4175).*

JeanPierre (Ann. Hum. Genet. (1992) 56:325-330).*

Fisher Scientific Catalog, p. 697, (1983).

Theo T. Nikiforov et al., "Genetic Bit Analysis: A Solid Phase Method for Typing Single Nucleotide Polymorphisms," *Nucleic Acids Research*, vol. 22, No. 20, pp. 4167-4175 (1994).

David J. Balding et al., "Statistical Analysis of DNA Fingerprint Data for Ordered Clone Physical Mapping of Human Chromosomes," *Bulletin of Mathematical Biology*, vol. 53, No. 6, pp. 853-879 (1991).

Mark Keating, M.D., "Linkage Analysis and Long QT Syndrome Using Genetics to Study Cardiovascular Disease," *Circulation*, vol. 85, No. 6 pp. 1973-1986 (1992).

Tosh, Yasunaka et al., "Determination of Gene Recombination Value," *Patent Abstracts of Japan*, vol. 018 215 (C-1191) (1994).

David C. Mansfield et al., "Automation of Genetic Linkage Analysis Using Fluorescent Microsatellite Markers," *Genomics*, vol. 24, pp. 225-233 (1994).

Mark D. Shriver et al., "VNTR Allele Frequency Distributions Under the Stepwise Mutation Model: A Computer Simulation Approach," *Genetics*, vol. 134, pp. 983-993 (1993).

M. Nata et al., "Prenatal paternity testing with DNA analyses," *Internation Journal of Legal Medicine*, vol. 106, pp. 160-162 (1993).

Colin P. Kimpton et al., "Automated DNA Profiling Employing Multiplex Amplification of Short Tandem Repeat Loci," *PCR Methods and Applications*, vol. 3, pp. 13-22 (1993).

W. Edward Highsmith, Jr., et al., "Frequency of the ΔPhe[508] Mutation and Correlation wtih XV.2c/KM-19 Haplotypes in an American Population of Cystic Fibrosis Patients: Result of a Collaborative Study," *Clin. Chem.*, vol. 36 No. 10, pp. 1741-1746 (1990).

Andrew G. Clark, "Inference of Haplotypes from PCR-amplified Samples of Diploid Populations," *J. Biol. Evol.*, vol. 7 No. 2, pp. 111-122 (1990).

W. Y. Tan, "On the Distribution of the Number of Mutants at the Hypoxanthine-Quanine Phosphoribosal Transferase Locus in Chinese Hamster Ovary Cells," *Mathematical Biosciences*, vol. 67, pp. 175-192 (1983).

Dempster, A.P.; Laird, N.M.; and Rubin, D.B., Maximum Likelihood from Incomplete Data via the *EM* Algorithm, *J. Roy. Statist. Soc.* 1977, pp. 1-38, vol. B39.

Little, R.J.A. and Rubin, D.B., *Statistical Analysis with Missing Data*, 1987, pp. 3-20 79-96, and 127-141, John Wiley & Sons.

Rozanov, Y.A. *Probability Theory: A Concise Course*, 1977, pp. 25-27, 36 Dover Publications, New York.

Bulmer, M.G. *Principles of Statistics*, 2nd ed., 1979 pp. 12-17, 22-28, 165-176 Dover Publications, New York.

White, R. and Lalouel, J-M., Chromosome Mapping with DNA Markers; Scientific American, Feb. 1988, pp. 40-48, vol. 258, No. 2.

Baird, M.L., "Quality control and quality assurance," in: Ballantyne, Sensabaugh, G., Wittkowski, J. (eds) "DNA Technology and forensic Science" (1989) 32 Banbury rpt., Cold Springs Lab Press, pp. 175-190.

Galbraith et al. "Sizing bands on autoradiograms: A Study of precision for scoring DNA fingerprints," (1991), Electrophoresis 12: 210-220.

Buckleton et al., "A continuous model for interpreting the positions of bands in DNA locus-specific work," JFSS 31 (3): 353-363.

Barth, Muhlbauer, Nikol, Worle, "Mathematische Formeln und Definitionen," Bayerischer Schulbuch-Verlag, Munich (1986) and J. Lindauer Verlag (Schaefer), Munich,pp. 110-111.

Kinghorn, B.P. Kennedy, B.W., Smith, C., "A Method of screening for genes of Major effect," Genetics (1993), 134: 351-360.

Syvanen, A.C., Aalto-Setala, K., Harju, L. Kontula, K., Soderlund, H., "A primer-guided nucleotide incorporation assay in genotyping of apolipoprotion E," (1990), Genomics 8:684-692.

Lander "Population Genetic Considerations in the Forensic Use of DNA Typing," in: Ballantyne, J., Sensabaugh, G., Wittkowski, J. (eds) "DNA Technology and Forensic science" (1989) Banbury report 32, Cold Spring Harbor Lab. Press, pp. 143-156.

Baird et al., "Allele Frequency Distribution of Two Highly Polymorphic DNA sequences in Three Ethnic Groups and Its Application to the Determination of Paternity," (1986) Am J. Hum Genet 39: pp. 489-501.

Committee on DNA Technology in Forensic Science "DNA Technology in Forensic Science", (1992) National Academy Press, Washington, D.C.

Kilbane, A.J. Silbart, L.K., Manis, M., Beitins, I.Z., Weber, W.W., "Human N-acetylation genotype determination with urinary caffeine matabolites," (1990) Clin. Pharma-col. Ther. 47: 470-477.

Griffiths, A.J.F., Miller, J.H., Suzuki, D.T., Lewontin, R.C., Gelbart, W.M., eds (1993) "An introduction to genetic analysis," 5th edition, W.H.Freeman and Company, New York; pp. 1-42, 425, 426, 456-459, 484-487, 703-732, and 737-749.

Gill, P. et al., "The analysis of hypervariable DNA profiles: problems associated with the objective determination of the probability of a match," *Human Genetics*, Jun. 1990, pp. 75-79, vol. 85.

Prober, J. M., et al., "A System for Rapid DNA Sequencing with Fluorescent Chain-Terminating Dideoxynucleotides," *Science*, Oct. 16, 1987, pp. 336-341, vol. 238.

Nickerson, D. A., et al., "Automated DNA diagnostics using an ELISA-based oligonucleotide ligation assay," *Proc. Natl. Acad. Sci. USA*, Nov. 1990, pp. 8923-8927, vol. 87.

Nickerson, D. A., et al., "Identification of Clusters of Biallelic Polymorphic Sequence-Tagged Sites (pSTSs) That Generate . . . ," *Genomics*, 1992, pp. 377-397, vol. 12.

Smith, L. M., et al., "Flourescence detection in automated DNA sequence analysis." *Nature*, Jun. 12, 1986, pp. 674-679, vol. 321.

Jeffreys, A.J. et al., "Hypervariable 'minisatellite' regions in human DNA," *Nature*, Mar. 7, 1985, pp. 67-73, vol. 314.

Baird, M., et al., "Allele Frequency Distribution of Two Highly Polymorphic DNA Sequences . . . ," *Am. J. Hum. Genet.*, 1986, pp. 489-501, vol. 39.

Lander, E., et al., "Strategies for studying heterogeneous genetic traits . . . ," *Proc. Natl. Acad. Sci. USA*, Oct. 1986, pp. 7353-7357, vol. 83.

Lander, E., et al., "Construction of multilocus genetic linkage maps in humans," *Proc. Natl. Acad. Sci. USA*, Apr. 1987, pp. 2363-2367, vol. 84.

Donis-Keller, H., et al., "A Genetic Linkage Map of the Human Genome," *Cell*, Oct. 23, 1987, pp. 319-337, vol. 51.

Paterson, A.H., et al., "Resolution of quantitative traits into Mendelian factors . . . ," *Nature*, Oct. 20, 1988, pp. 721-726, vol. 335.

Lander, E., et al., "Mapping Mendelian Factors Underlying Quantative Traits . . . ," *Genetics*, Jan. 1989, pp. 185-199, vol. 121.

Griffiths, A. J. F., et al., *An Introduction to Genetic Analysis*, Fifth ed., 1993, pp. 750-752 (W.H. Freeman and Company, New York).

Stryer, L., Biochemistry, 3rd edition, (1988), p. 169, W.H. Freeman and Company, New York.

Botstein, D., White, R. L., Skolnick, M., and Davis, R. W., "Construction of a Genetic Linkage Map in Man Using Restriction Fragment Length Polymorphisms," American Journal of Human Genetics, (1980), pp. 314-331, vol. 32.

van Arendonk, J. A. M., Smith, C., and Kennedy, B. W., "Method to estimate genotype probabilities at individual loci in farm livestock," Theoretical and Applied Genetics, (1989), pp. 735-740, vol. 78.

M.C. Giddings, et al. "An adaptive, object oriented strategy for base calling in DNA sequence analysis,". Nucleic Acids Research, 1993, pp. 4530-4540, vol. 21, No. 19, Oxford University Press.

Notice of Opposition (Dec. 19, 2003) Beckman Coulter, Inc.

Note of Registration of the Library of the University of Tubingen, including letter to Dr. Misera, Enclosure 2 (journal 33 B 1194) (Jan. 5, 2004) Beckman Coulter, Inc.

Patentee's Response to Opposition (Nov. 2004) Beckman Coulter, Inc.

Minutes of the Oral Proceedings Before the Opposition Division (Jan. 18, 2006).

Interlocutory Decision in Opposition Proceedings (Mar. 7, 2006) European Patent Office.

Statement of Grounds of Appeal (Jul. 14, 2006) Roche Diagnostics GmbH.

Patentees Grounds of Appeal (Jul. 17, 2006) Beckman Coulter, Inc.

Reply to Patentee's Statement Setting out the Grounds of Appeal dated Jul. 17, 2006 (Nov. 30, 2006) Roche Diagnostics GmbH.

Patentee's Response to Opponent's Appeal (Nov. 29, 2006) Beckman Coulter, Inc.

* cited by examiner

| LOCUS# | SUBJECT# | X-VALUE | Y-VALUE | GENOTYPE | CONFIDENCE |
|---|---|---|---|---|---|
| 177 | 213-a01 | 0.176 | 1.688 | TT | 8.15 |
| 177 | 213-a02 | 0.11 | 2.303 | TT | 9.41 |
| 177 | 213-a03 | 0.399 | 0.575 | CT | 2.93 |
| 177 | 213-a04 | 1.02 | 1.492 | CT | 9.85 |
| 177 | 213-a05 | 0.971 | 1.557 | CT | 9.99 |
| 177 | 213-a06 | 0.91 | 1.513 | CT | 10 |
| 177 | 213-a07 | 0.165 | 1.604 | TT | 8.33 |
| 177 | 213-a08 | 1.168 | 0.173 | CC | 8.33 |
| 177 | 213-a09 | 0.158 | 1.573 | TT | 8.47 |
| 177 | 213-a10 | 1.429 | 0.046 | CC | 9.44 |
| 177 | 213-a11 | 1.365 | 0.047 | CC | 9.46 |
| 177 | 213-a12 | 0.186 | 0.35 | NS | 1.93 |
| 177 | 213-b01 | 0.367 | 0.302 | CT | 0.03 |
| 177 | 213-b02 | 0.193 | 2.019 | TT | 8.03 |
| 177 | 213-b03 | 0.138 | 2.039 | TT | 8.97 |
| 177 | 213-b04 | 0.913 | 1.618 | CT | 9.99 |
| 177 | 213-b05 | 0.152 | 2.111 | TT | 8.74 |
| 177 | 213-b06 | 0.308 | 0.261 | NS | 1.2 |
| 177 | 213-b07 | 0.234 | 1.825 | TT | 7.14 |
| 177 | 213-b08 | 0.787 | 1.321 | CT | 10 |
| 177 | 213-b09 | 0.746 | 1.481 | CT | 9.73 |
| 177 | 213-b10 | 1.018 | 1.423 | CT | 9.72 |
| 177 | 213-b11 | 0.897 | 1.775 | CT | 9.83 |
| 177 | 213-b12 | 1.223 | 0.054 | CC | 9.44 |
| 177 | 213-c01 | 0.308 | 0.513 | CT | 0.91 |
| 177 | 213-c02 | 1.594 | 0.061 | CC | 9.29 |
| 177 | 213-c03 | 1.487 | 0.046 | CC | 9.42 |
| 177 | 213-c04 | 0.191 | 1.998 | TT | 8.05 |
| 177 | 213-C05 | 1.395 | 0.053 | CC | 9.4 |
| 177 | 213-c06 | 0.8 | 1.551 | CT | 9.79 |
| 177 | 213-c07 | 0.244 | 1.973 | TT | 7.08 |
| 177 | 213-c08 | 0.504 | 0.706 | CT | 4.46 |
| 177 | 213-c09 | 0.243 | 1.977 | TT | 7.11 |
| 177 | 213-c10 | 0.96 | 1.831 | CT | 9.94 |
| 177 | 213-c11 | 1.43 | 0.068 | CC | 9.27 |
| 177 | 213-c12 | 0.824 | 1.369 | CT | 10 |

FIG.8

AUTOMATIC GENOTYPE DETERMINATION

CROSS REFERENCE TO RELATED APPLICATIONS

This application is a continuation of application Ser. No. 09/088,820, which is a continued prosecution application of application Ser. No. 09/088,820, filed Jun. 2, 1998, which is a continuation of application Ser. No. 08/362,266, filed Dec. 22, 1994, which is a continuation in part of application Ser. No. 08/173,173, filed Dec. 23, 1993, which is for an invention entitled "Automatic Genotype Determination," by Stephen E. Lincoln and Michael P. Knapp. This immediate parent application (application Ser. No. 08/173,173) is a continuation in part of application Ser. No. 07/775,786, filed Oct. 11, 1991, for an invention entitled "Nucleic Acid Typing by Polymerase Extension of Oligonucleotides using Terminator Mixtures," by P. Goelet, M. Knapp, and S. Anderson, which in turn is a continuation in part of application Ser. No. 07/664,837, filed Mar. 5, 1991. Immediate parent application Ser. No. 08/173,173 is also a continuation in part of application Ser. No. 08/162,397, filed Dec. 6, 1993, for an invention entitled "Method for Immobilization of Nucleic Acid Molecules" by T. Nikiforov and M. Knapp, and of application Ser. No. 08/155,746, filed Nov. 23, 1993, for an invention entitled "Method for Generating Single-Stranded DNA Molecules" by T. Nikiforov and M. Knapp, and of application Ser. No. 08/145,145, filed Nov. 3, 1993, for an invention entitled "Single Nucleotide Polymorphisms and their use in Genetic Analysis" by M. Knapp and P. Goelet. All of these related applications are hereby incorporated herein by reference.

TECHNICAL FIELD

The present invention relates to the methods and devices for determining the genotype at a locus within genetic material.

SUMMARY OF THE INVENTION

The present invention provides in one embodiment a method of determining the genotype at a locus within genetic material obtained from a biological sample. In accordance with this method, the material is reacted at the locus to produce a first reaction value indicative of the presence of a given allele at the locus. There is formed a data set including the first reaction value. There is also established a set of one or more probability distributions; these distributions associate hypothetical reaction values with corresponding probabilities for each genotype of interest at the locus. The first reaction value is applied to each probability distribution to determine a measure of the conditional probability of each genotype of interest at the locus. The genotype is then determined based on these measures.

In accordance with a further embodiment of this method, the material at the locus is subject to a second reaction to produce a second reaction value independently indicative of the presence of a second allele at the locus. A second data set is formed and the second reaction value is included in the second data set. Each probability distribution associates a hypothetical pair of first and second reaction values with a single probability of each genotype of interest. The first data set includes other reaction values obtained under conditions comparable to those under which the first reaction value was produced, and the second data set includes other reaction values obtained under conditions comparable to those under which the second reaction value was produced. Where, for example, there are two alleles of interest, the first reaction may be an assay for one allele and the second reaction may be a distinct assay for the other allele. The first and second data sets may include reaction values for the first and second reactions respectively, run under comparable conditions on other, samples with respect to the same locus. Alternatively, or in addition, the data sets may include reaction values for reactions run under comparable conditions with respect to different loci within the same sample.

In accordance with a further embodiment, the probability distributions may be determined iteratively. In this embodiment, each probability distribution is initially estimated. Each initial probability distribution is used to determine initial genotype probabilities using the reaction values in the data sets. The resulting data are then used to modify the initial probability distribution, so that the modified distribution more accurately reflects the reaction values in the data set. This procedure may be iterated a desired number of times to improve the probability distribution. In practice, we have generally found that a single iteration is sufficient.

The foregoing methods have been employed with success for automatic genotype determination based on assays using genetic bit analysis (GBA). In such a case, each allele may typically be a single specific nucleotide. In accordance with GBA, a reaction is designed to produce a value that is indicative of the presence of a specific allele at the locus within the genetic material. In GBA, the approach is typically to hybridize a specific oligonucleotide to the genetic material at the locus immediately adjacent to the nucleotide being interrogated. Next, DNA polymerase is applied in the presence of differentially labelled dideoxynucleoside triphosphates. The read-out steps detect the presence of one or more of the labels which have become covalently attached to the 3' end of the oligonucleotide. Details are provided in Theo R. Nikiforov et al. "Genetic Bit Analysis, a solid phase method for typing single nucleotide polymorphisms," 22 *Nucleic Acids Research*, No. 20, 4167-4175 (1994), which is hereby incorporated herein by reference. However, the present invention is also applicable to other reaction systems for allele determination, such as allele-specific hybridization (ASH), sequencing by hybridization (CBH), oligonucleotide ligase assay (OLA), and allele-specific amplification, using either the ligase chain reaction (LCR) or the polymerase chain reactions (PCR). The alleles assayed may be defined, for example, by a single nucleotide, a pair of nucleotides, a restriction site, or (at least in part) by its length in nucleotides.

In another embodiment of the invention, there is provided a method of determining the genotype of a subject by reacting genetic material taken from the subject at selected loci. In this embodiment, each locus may be an identified single nucleotide or group of nucleotides, and there is produced with respect to each of the selected loci a reaction value indicative of the presence of a given allele at each of the selected loci. These reaction values are used to determine the genotype of the subject or alternatively a DNA sequence associated with a specific region of genetic material of the subject. (Indeed a set of genotypes for selected proximal loci may be used to specify a sequence of the genetic material.) In further embodiments, the loci are selected to provide one or more types of information concerning the subject, including inheritance of a trait, parentage, identity, and matching tissue with that of a donor. Alternatively, the loci may be spaced throughout the entire genome of subject to assist in characterizing the genome of the species of the subject.

In a further embodiment of the invention, there is provided a device for determining the genotype at a locus within genetic material obtained from a subject. The device of this embodiment has a reaction value generation arrangement for producing a first physical state, quantifiable as a first reaction value, indicative of the presence of a given allele at the locus, the value associated with reaction of the material at the locus. The device also has a storage arrangement for storing a data set including the first reaction value and other reaction values obtained under comparable conditions. A distribution establishment arrangement establishes a set of probability distributions, including at least one distribution, associating hypothetical reaction values with corresponding probabilities for each genotype of interest at the locus. A genotype calculation arrangement applies the first reaction value to each pertinent probability distribution to determine the conditional probability of each genotype of interest at the locus. A genotype determination arrangement determines the genotype based on data from the genotype calculation arrangement.

In a further embodiment, the device may determine the genotype at selected loci. In this embodiment, the reaction generation arrangement can produce a reaction value indicative of the presence of a given allele at each of the selected loci and the data set includes reaction values obtained with respect to each of the selected loci. The genotype calculation arrangement applies reaction values obtained with respect to each of the selected loci to each pertinent probability distribution.

In another further embodiment, the device may determine the genotype at a locus within genetic material from each of a plurality of samples. In this embodiment, the reaction generation arrangement can produce a reaction value indicative of the presence of a given allele at the locus of material obtained from each sample and the data set includes reaction values obtained with respect to each sample. The genotype calculation arrangement applies reaction values obtained with respect to each sample to each pertinent probability distribution.

In each of these embodiments the reaction value generation arrangement may also include an arrangement for producing a second reaction value, independently indicative of the presence of a second allele at the locus. The storage arrangement then includes a provision for storing the second reaction value and other reaction values obtained under comparable conditions. The genotype calculation arrangement applies the first and second reaction values to each pertinent probability distribution to determine the probability of each genotype of interest at the locus. Each probability distribution may be of the type associating a hypothetical pair of first and second reaction values with a single probability of each genotype of interest. The locus may be a single nucleotide, and the reaction value generation arrangement may include an optical transducer to read reaction results and may determine, on a substantially concurrent basis, the reaction values with respect to each sample.

The distribution establishment arrangement may be configured to assign an initial probability distribution to the data set that would associate hypothetical reaction values with corresponding probabilities for each genotype of interest at the locus. The distribution establishment arrangement then invokes the genotype calculation means to use each initial probability distribution to determine initial conditional probabilities for a genotype of interest at the locus. Thereafter the distribution establishment arrangement modifies each initial probability distribution, so that each modified distribution more accurately reflects the reaction values stored in the storage means.

The term "reaction value" as used in this description and the following claims may refer either to a single numerical value or to a collection of numbers associated with a physical state produced by the reaction. In the GBA method described in the Nikiforov article referred to above, e.g., optical signals are produced that may be read as a single numerical value. Alternatively, e.g., an optical signal may be simplified over time, and the reaction value may be the collection of samples of such a signal. It is also possible to form a scanned image, of one or a series of optical signals generated by GBA or other reaction methods, and to digitize this image, so that a collection of pixel values in all or a portion of the image constitutes a reaction value.

BRIEF DESCRIPTION OF THE DRAWINGS

The foregoing aspects of the invention will be more readily understood by reference to the following detailed description, taken with respect to the following drawings, in which:

FIG. 8 is an example of the output of the device in FIG. 1.

DETAILED DESCRIPTION OF SPECIFIC EMBODIMENTS

The invention provides in preferred embodiments a method and device for genotype determination using genetic marker systems that produce allele-specific quantitative signals. An embodiment uses computer processing, employing computer software we developed and call "GetGenos", of data produced by a device we also developed to produce GBA data. The device achieves, among other things, the following:

Fully automatic genotype determination from quantitative data. Off-line analysis of data pools is intended, although the software is fast enough to use interactively.

Ability to examine many allele tests per DNA sample simultaneously. One genotype and confidence measure are produced from these data.

A true probabilistic confidence measure (a LOD score), properly calibrated, is produced for each genotype.

Use of robust statistical methods: Noise reduction via selective data pooling and simultaneous search over points in a data pool, preventing bias.

Maximal avoidance of arbitrary parameters, and thus insensitivity to great variation in input data. The small number of parameters that are required by the underlying statistical model are fit to the observed data, essentially using the data set as its own internal control.

Flexibility for handling multiple data types. Essentially, only probability distribution calculations, described below, need to be calibrated to new data types. We expect that the invention may be applied to GBA, OLA, ASH, and RAPD-type markers.

Our current embodiment of the software is implemented in portable ANSI C, for easy integration into a custom laboratory information system. This code has been successfully run on:

Macintosh
Sun
MS-DOS
MS-Windows

In our current embodiment of the software, a number of consistency checks are performed for GBA data verification, using both the raw GBA values and the control wells. Overall statistics for trend analysis and QC are computed. Brief "Genotype Reports" are generated, summarizing results for each data set, including failures. All data are output in a convenient form for import into interactive statistical packages, such as DataDesk™. The current implementation is presently restricted to 2-allele tests in diploids—the situation with present GBA applications.

Figure 1:
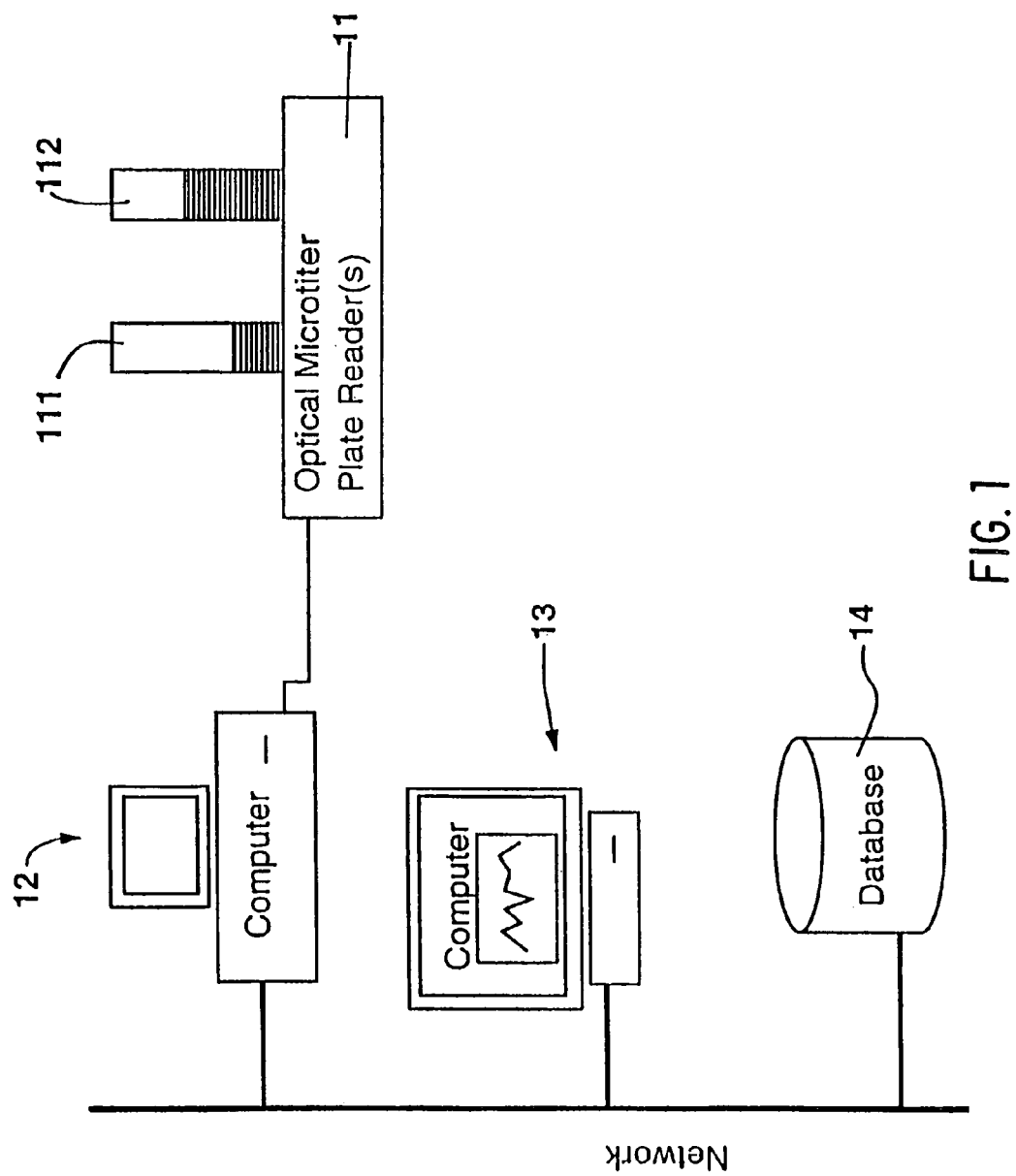
FIG. 1 is a diagram of a device in accordance with a preferred embodiment of the invention.

Referring to FIG. 1, there is shown a preferred embodiment of a device in accordance with the present invention. The device includes an optical detector 11 to produce reaction values resulting from one or more reactions. These reactions assay for one or more alleles in samples of genetic material. We have implemented the detector 11 using bichromatic microplate reader model 348 and microplate stacker model 83 from ICN Biomedical, Inc., P.O. Box 5023, Costa Mesa, Calif. 92626. The microplates are in a 96 well format, and the reader accommodates 20 microplates in a single processing batch. Accordingly the device of this embodence permits large batch processing. The reactions in our implementation use GBA, as described above. The detector 11 is controlled by computer 12 to cause selected readout of reaction values from each well. The computer 12 is programmed to allow for multiple readout of the reaction value from a given well over a period of time. The values are stored temporarily in memory and then saved in database 14. Computer 13 accesses the database 14 over line 15 and processes the data in accordance with the procedure described below. Of course, computers 12 and 13 and database 14 may be implemented by an integral controller and data storage arrangement. Such an arrangement could in fact be located in the housing of the optical detector 11.

Figure 2:
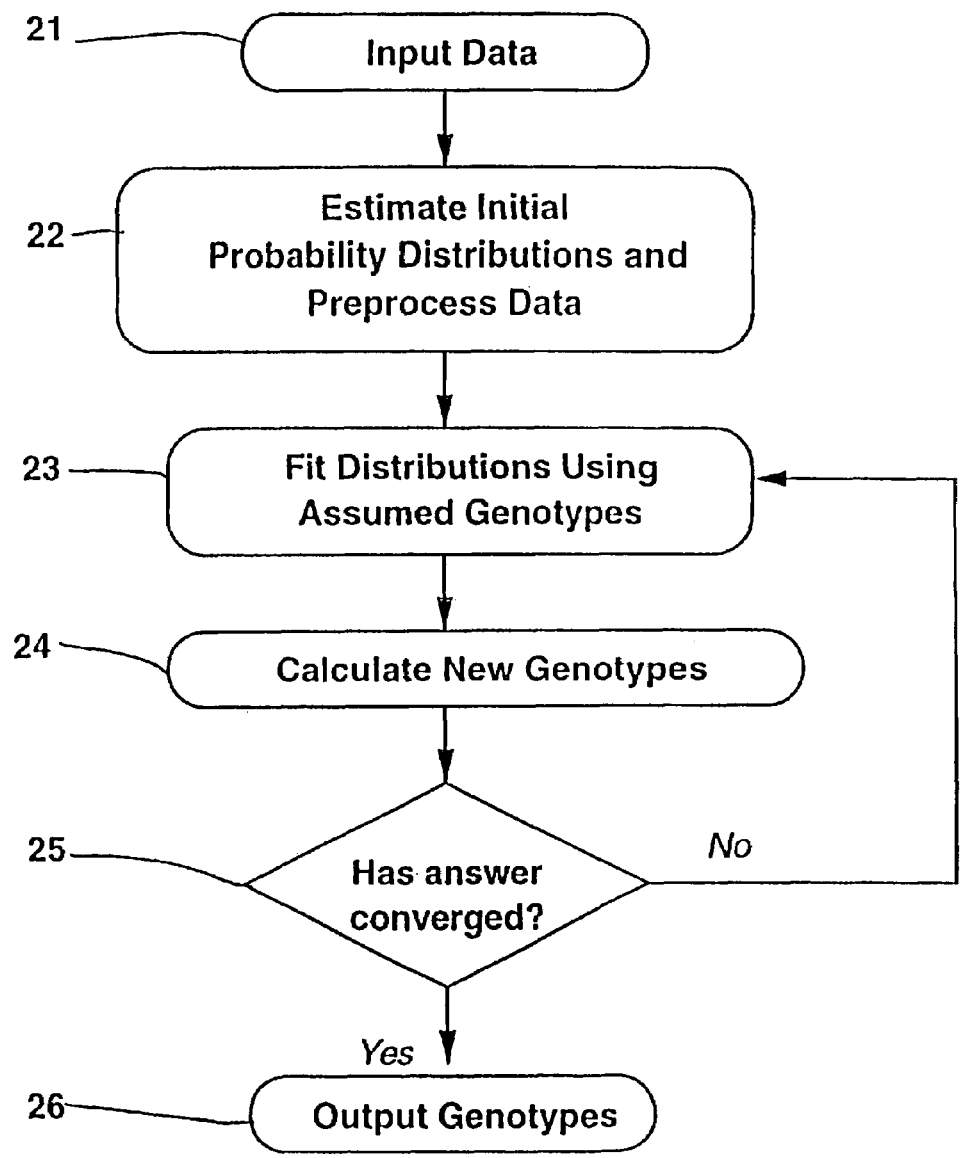
FIG. 2 is a diagram of the logical flow in accordance with the embodiment of FIG. 1.

In FIG. 2 is shown the procedure followed by computer 13. The steps of this procedure are as follows:

Input Data: A set of data is loaded under step 21. In most applications, each experiment in the set should be testing (i) the same genetic marker, and (ii) the same set of alleles of that marker, using comparable biochemistry (e.g. the same reagent batches, etc.). Large data sets help smooth out noise, although the appropriate size of a data set depends on the allele frequencies (and thus the number of expected individuals of each genotypic class). Each data point in the input data may be thought of as an N-tuple of numeric values, where N is the number of signals collected from each DNA sample for this locus. (N will usually be the number of alleles tested at this marker, denoted A, except when repeated testing is used, in which case N may be greater than A).

Preprocess Data: Next the data are subject to preprocessing (step 22). An internal M-dimensional Euclidean representation of the input signals is produced, where each input datum (an N-tuple) is a point in M-space. Usually, M will be the same as N and the coordinates of the point will be the values of the input tuple, and thus the preprocessing will be trivial (although see the first paragraph of variations discussed). The Euclidean space may be non-linear, depending on the best available models of signal generation. (Completely mathematically equivalently, any non-linearity may be embodied in the initial probability distributions, described below.)

Figure 3:
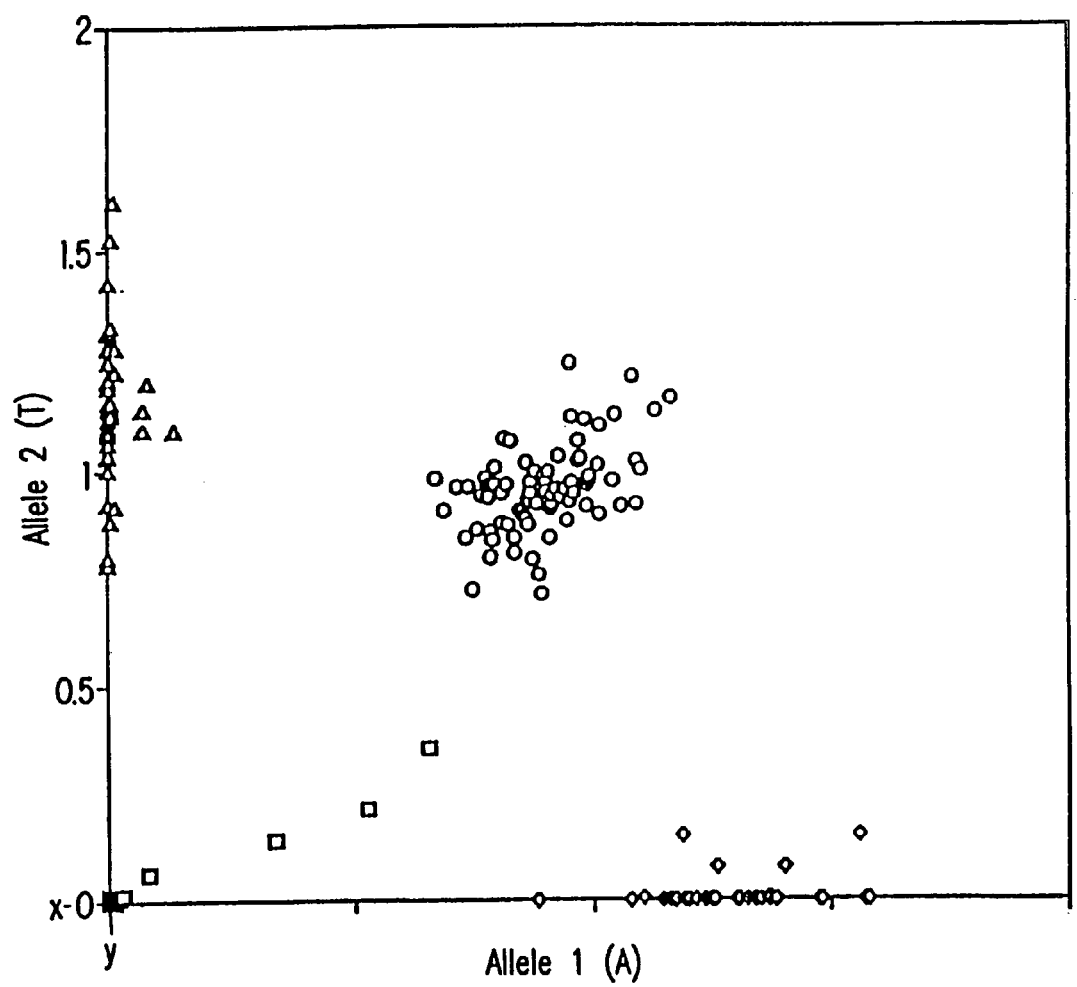
FIG. 3 is a graph of numeric reaction values (data) generated by the embodiment of FIG. 1 as well as the genotype determinations made by the embodiment from these data.
Figure 4:
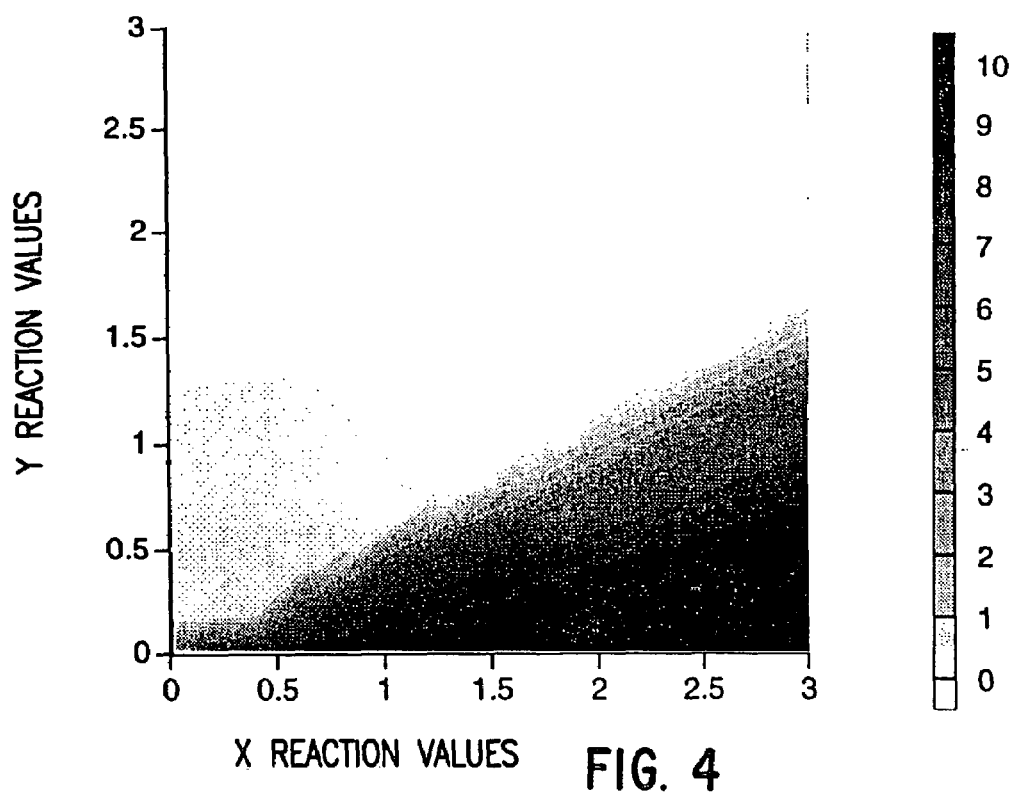
FIGS. 4-7 show probability distributions derived by the embodiment of FIG. 1 for three genotypes of interest (AA, AT, and TT) and a failure mode at a locus.
Figure 5:
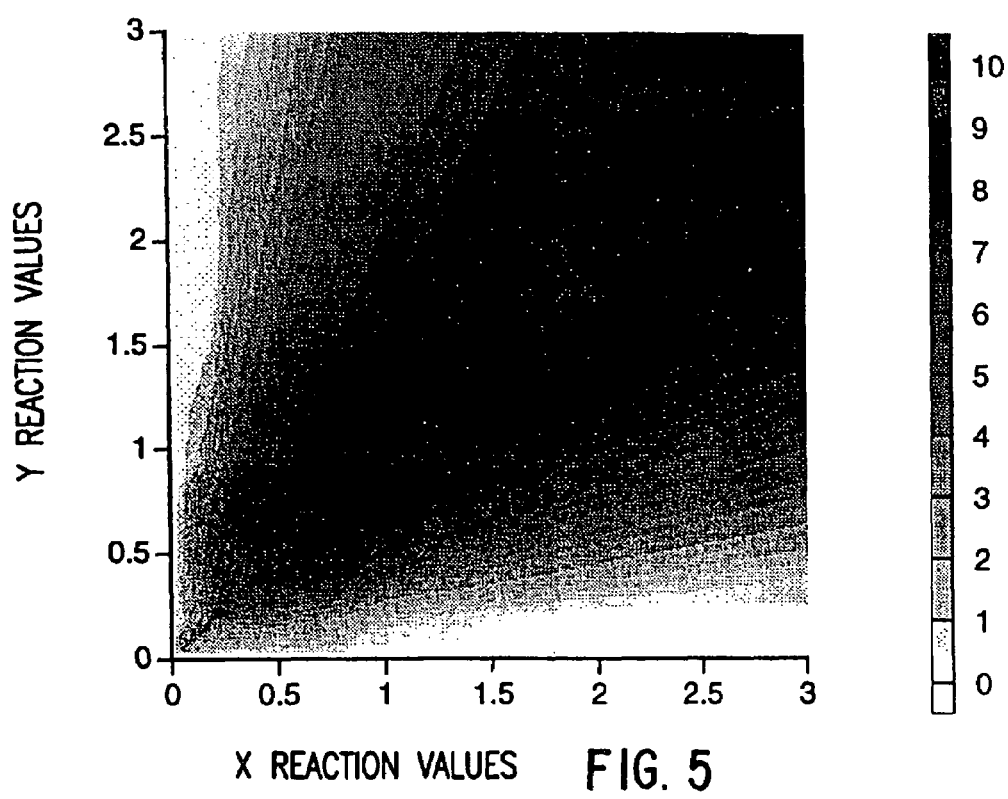
Figure 6:
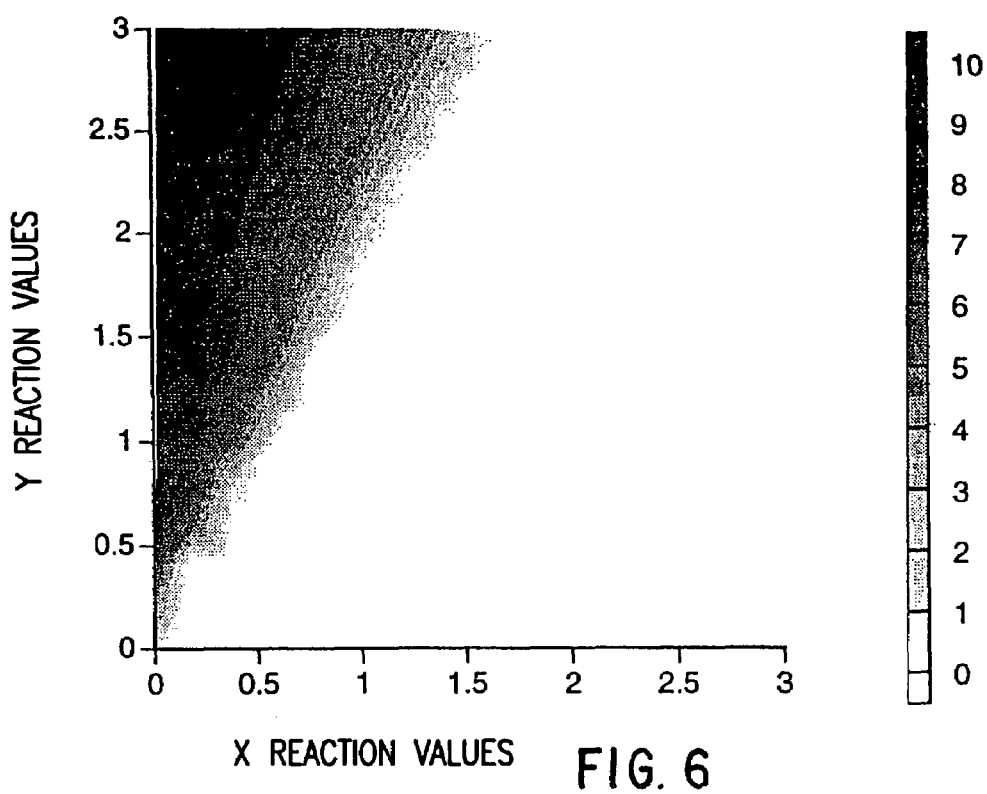
Figure 7:
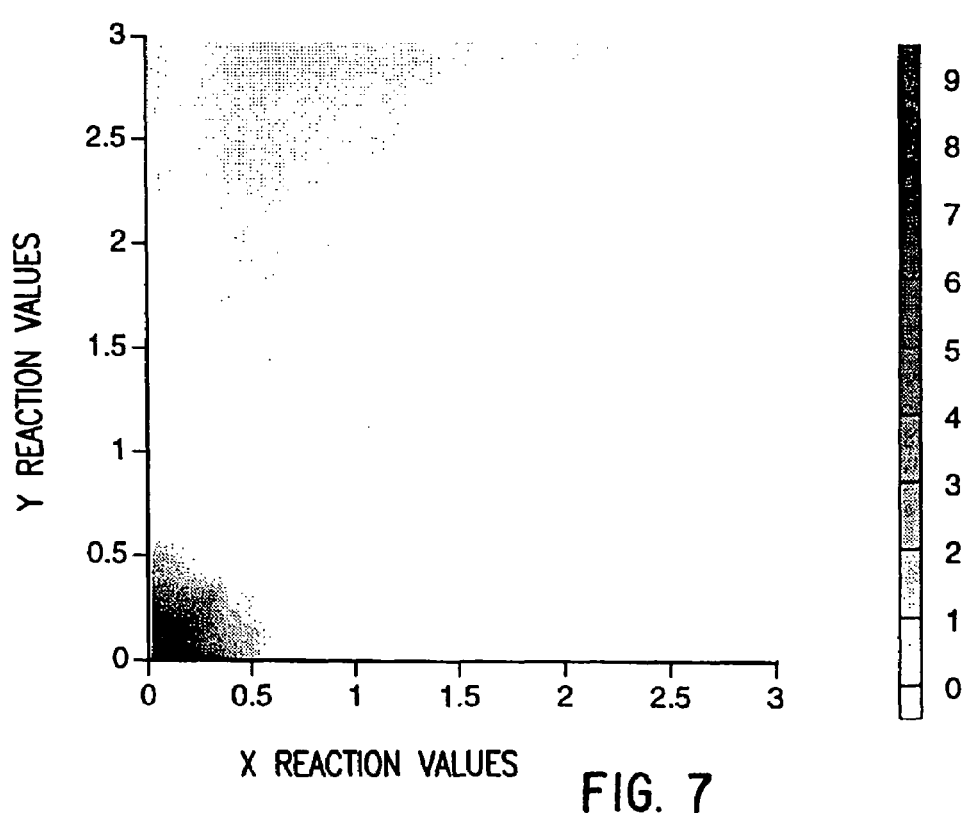

FIG. 3 illustrates preprocessed reaction values from step 22 for GBA locus 177-2 on 80 DNA samples. The X-axis indicates preprocessed reaction values for allele 1 (A) and the Y-axis indicates preprocessed reaction values for allele 2 (T). For clarity, the results of genotype determination are also indicated for each point: Triangles are TT genotype, diamonds are AA, circles are AT, and squares are failures (no signal).

Probability Distributions: Returning to FIG. 2, under step 22, initial probability distributions are established for the G possible genotypes. For example, in a random diploid population containing A tested alleles:

$$G = (A) + (A-1) + \ldots + 1 = \frac{A(A+1)}{2} \quad (1)$$

The initial conditional probability for any hypothetical input datum (a point in M-space, denoted $X_i$) and genotype (denoted g) is defined as the prior probability of seeing the signal $X_i$ assuming that g is the correct genotype of that datum. That is:

$$Pr(\text{signal } x_i \cdot \text{Genotype} = g), \quad \text{where } x_i = (x_1^1 \ldots x_1^M) \text{ and } g \cdot \{1 \ldots G\} \quad (2)$$

FIGS. 4 through 7 illustrate the initial probability distributions established for the data in FIG. 3. Probability distributions are indicated for the four genotypic classes of interest, AA, AT, TT and No Signal, in FIGS. 4, 5, 6, and 7 respectively. The shading at each XY position indicates probability, with darker shades indicating increased probability for hypothetical data points with those X and Y reaction valves.

Exactly where these distributions come from is highly specific to the nature of the input data. The probability distributions can either be pre-computed at this step and stored as quantized data, or can be calculated on the fly as needed in step 23, below. The probability distributions may be fixed, or may be fit to the observed data or may be fit to assumed genotypes as determined by previous iterations of this algorithm. (See Additional Features below.)

Under step 23, we compute the conditional probability of each genotype. For each datum $X_i$, the above probabilities are collected into an overall conditional posterior probability of each genotype for that datum:

$$Pr(\text{Genotype} = g \mid \text{Signal } x_i) = \quad (3)$$
$$\frac{Pr(\text{Signal } x_i) \mid \text{Genotype} = g) \cdot Pr(\text{Genotype} = g)}{Pr(\text{Signal } x_i)}$$

where

Pr(Genotype=g) is the prior probability of any datum having genotype g;

Pr(Signal $X_i$) is the prior probability of the signal (a constant which may be ignored); and Pr(Signal $X_i$)·Genotype=g) is the initial probability defined above.

Under step 24, we determine the select the genotype and compute the confidence score. For each datum, using the above posterior probabilities, we determine the most likely genotype assignment g' (the genotype with the highest pos terior probability) and its confidence score. The confidence score C is simply the boa of the odds ratio:

$$C = \log_{10} \frac{Pr(\text{Genotype} = g' \mid \text{Signal } x_i)}{\sum_{\text{Genotypes } g} Pr(\text{Genotype} = g \cdot \text{Signal } x_i)} \quad (4)$$

It should be noted that this procedure is significant, among other reasons, because it permits determining a robust probabalistic confidence score associated with each geno type determination.

Under step 25, there may be employed adaptive fitting. A classic iterative adaptive fitting algorithm, such as Estimation-Maximization (E-M), may be used to increase the ability to deal with highly different input data sets and reduce noise sensitivity. In this case, the genotypes computed in step 24 are used to refit the distributions (from step 22). In step 25, a convergence test is performed, which may cause the program to loop back to step 23, but now using the new distributions.

As one example, an E-M search procedure may be used to maximize the total likelihood, that is, to find the maximally likely set of genotype assignments given the input data set. (The net likelihood may be calculated from the Baysean probabilities, defined above.) For appropriate likelihood calculations and probability distributions, the EM principle will guarantee that this algorithm always produces true-maximum-likelihood values, regardless of initial guess, and that it always converges.

Output Data: Under step 26, we output the results (genotypes and confidence scores) to the user or to a computer database. An example of such output is shown in FIG. 8.

Additional Features

Additional features may be incorporated into the above procedure. They may be integrated into the procedure either together or separately, and have all been implemented in a preferred embodiment.

Preprocessing: During steps 21 or 22, the data (either input tuples or spatial data points) may be preprocessed in order to reduce noise, using any one of many classical statistical or signal-processing techniques. Control data points may be used in this step. In fact, various types of signal filtering or normalizing may be applied at almost any step in the algorithm.

Fitting Probability Distributions: The probability distributions calculated in steps 22 and 23 may be fit to the input data—that is, each distribution may be a function of values which are in part calculated from the input data. For example, we may define the conditional probability of a signal point for some genotype to be a function of the distance between that point and the observed mean for that signal.

Using an Initial Genotype Guess: In step 22, either a simple or heuristic algorithm may be used to produce an initial genotype guess for each input data point. If a fairly accurate guess can be produced, then the probability distributions for each genotype may be fit to the subset of the data assumed to be of that genotypic class. Another use of a genotype guess is in initial input validity checks and/or preprocessing (e.g. Step 22), before the remainder of the algorithm is applied. To be useful, a guess need not produce complete genotypic information, however.

Using a Null Genotypic Class: In steps 22 and all further steps, one (or more) additional probability distributions may be added to fit the data to the signals one would expect to see if an experiment (e.g. that datum) failed. E.g., $$Pr(\text{signal } X_i \cdot \text{Genotype} \cdot \{1 \ldots G\})$$

The current implementation above is presently restricted to M=2 and N=2*R, where R is the number of repeated tests of both alleles. We refer to the two alleles as X and Y. The program understands the notion of "plates" of data, a number of which make up a data set.

The Initial Guess Variation is employed to initially fit distributions using the heuristic described below. The Initial Guess is produced during the Preprocessing Step which normalizes and background subtracts the input data, and remove apparent outlier points as well. These steps are performed separately for each allele's signal (i.e., 1 dimensional analysis). In fact, this preprocessing is applied separately to each of the R repeated tests, and the test with the small total 2 dimension residual is chosen for use in further steps. Various other preprocessing and post-processing steps are employed for GBA data validation and QC. In particular, controls producing a known reaction value may be employed to assure integrity of the biochemical process. In a preferred embodiment, signals are assumed to be small positive numbers (between 0.0 and 5.0, with 0.0 indicating that allele is likely not present in the sample, and larger values indicating that it may be.

To handle a wide range of input data signal strengths, the Adaptive Fitting Variation is employed. However, the program is hard-coded to perform exactly one or two interactions passes through step 25, which we find works well for existing GBA data.

The probability distributions we fit at present in steps 22 and 25 have as their only parameters (i) the ratio of the X and Y signals for heterozygotes, and (ii) the variance from the normalized means (0.0 negative for that allele, 1.0 for positive for that allele) along each axis separately. In fact, these later numbers are constrained to be at least a fixed minimum, which is rarely exceeded, so that the algorithm will work with very small quantities of data and will produce the behavior we want. These numbers are computed separately for each microtiter plate. The probability distributions are generated using the code (written in C) attached hereto and incorporated herein by reference as Appendix A.

The Null-Class variant is used to provide genotypic class indicating No Signal.

Quality control may also be enhanced in a surprising manner using the procedures described here. In particular, the confidence score C of equation (4) serves as a robust indicator of the performance of the biochemical reaction system. For example, a downward trend in the confidence scores within a single batch or in successive batches may indicate deterioration of an important reagent or of a sample or miscalibration of the instrumentation.

Accordingly, in a preferred embodiment, the computer may be used to determine the presence of a downward trend in the confidence score over time calculated in reference to each of the following variables: the locus (is there a downward trend in the confidence score of a single locus relative to other loci tested?), the sample (is there a downward trend in the confidence score of a single sample relative to other samples tested?), plate (is there a downward trend in the confidence score of this plate relative to other plate?), and batch (relative to other batches). If a downward trend of statistical significance (using, for example a chi square test) is detected, an alarm condition is entered.

Because the confidence score is an accurate indication of the reliability of the reaction system and the genotype determination, a low confidence score associated with a given determination is taken as indicating the need for retesting.

APPENDIX A

```
/* The probability distributions in FIGS. 4, 5, 6, and 7, respec-
   tively, correspond to the values of xx_prob, xy_prob,
   yy_prob, and ns_prob, for all possible values of the pre-
   processed reaction values (x_val and y_val) in the range of
   interest (0.0 to 3.0). */

/* We assume that the following global variables are set ... */ double x_pos_mean, x_neg_mean, y_pos_mean, y_neg_
mean;

double x_val, y_val;

/* And we set the following globals ... */ double xx_prob, xy_prob, yy_prob, ns_prob;

define POS_VARIANCE 0.25 define POS_VARIANCE_INCREMENT 0.00 define NEG_VARIANCE 0.05 define NEG_VARIANCE_INCREMENT 0.10 define HET_VARIANCE 0.10 define HET_VARIANCE_INCREMENT 0.20 define COND_NEG_PROB(val, given_val, val_mean)\
    normal_prob(val_mean-val,         NEG_VARIANCE
NEG_VARIANCE_INCREMENT*given_val)

#define COND_HET_PROB(val, given_val)\
    normal_prob(given_val-val,    HET_VARIANCE+HET_
VARIANCE_INCREMENT)

double normal_prob(deviation, sigma)
double deviation, sigma;
{
    double            val=exp(-(deviation*deviation)/
        (2.0*sigma*sigma));
    return (val>=TINY_PROB? val: TINY_PROB);
} void compute probs{ }
{
    double x_pos_prob, y_pos_prob, x_neg_prob, y_neg_
        prob;
    x_pos_prob=normal_prob((x_pos_mean-x_val),   POS_
        VARIANCE);
    x_neg_prob=normal_prob((x_neg_mean-x val),   NEG_
        VARIANCE);
    y_pos_prob=normal_prob((y_pos_mean-y_val),   POS_
        VARIANCE);
    y_neg_prob=normal_prob((y_neg_mean-y_val),   NEG_
        VARIANCE);
    ns_prob=max(x_neg_prob*COND_NEG_PROB(y_val,
        x_val, y_neg_mean),
        y_neg_Prob*COND_NEG_PROB(x_val,        y_val,
            x_neg_mean));
    xx_prob=x_pos_prob*COND_NEG_PROB(y_val, x_val,
        y_neg_mean);
    yy_prob=y_pos_prob*COND_NEG_PROB(x_val, y_val,
        x_neg_mean);
    xy_prob=max(x_pos_prob*COND_HET_PROB(y_val,
        x_val),
        y_pos_prob*COND_HET_PROB(x_val, y_val));
}
```

What is claimed is:

1. A method of determining the genotype of a subject at a locus within genetic material obtained from a biological sample from the subject, the method comprising:

(A) reacting the material from said biological sample at the locus to produce a first reaction value indicative of the presence of a first allele at the locus within said genetic material, wherein the first reaction value is a measure of the intensity of a first allele-specific quantitative signal;

(B) reacting the material from said biological sample at the locus to produce a second reaction value indicative of the presence of a second allele at the locus within said genetic material, wherein the second reaction value is a measure of the intensity of a second allele-specific quantitative signal;

(C) calculating a set of probability distributions from a set of input data, wherein said set of input data is obtained under conditions that are comparable to the conditions under which the first reaction value and the second reaction value are obtained wherein said set of probability distributions comprises at least one probability distribution, that associates a hypothetical first reaction value and a hypothetical second reaction value with a corresponding probability for each a genotype of interest at the locus;

(D) applying the first reaction value of step (A) and the second reaction value of step (B) to each probability distribution for each genotype of interest within said set of probability distributions of step (C) to determine a measure of a conditional probability of each genotype of interest at the locus, wherein the conditional probability is a measure of the likelihood of the genotype of interest at the locus given the first reaction value of step (A) and the second reaction value of step (B); and (E) determining the genotype of said subject at the locus based on the measure of conditional probability of step (D) of each genotype of interest at the locus for said subject, wherein each allele is a single specific nucleotide.

2. A method according to claim 1, wherein the set of probability distributions of step (C) includes a plurality of probability distributions for a corresponding plurality of genotypes of interest.

3. A method according to claim 1, wherein step (E) further includes a step of calculating a confidence scorer associated with the determination of the genotype in step (E), based on the measure of conditional probability from step (D).

4. A method according to claim 1, wherein step (E) further includes a step of calculating a confidence score associated with the determination of the genotype in step (E), based on the measure of conditional probability from step (D), and the method further comprising:

determining whether a significant downward trend in confidence scores has occurred, and, in such event, entering an alarm condition.

5. A method according to claim 1, wherein step (A) and step (B) each include a step of assaying for the given allele using genetic bit analysis, allele-specific hybridization, or allele-specific amplification, including such amplification by a polymerase chain reaction or a ligase chain reaction.

6. A method according to claim 1 wherein step (A) includes the step of hybridizing a first oligonucleotide probe to the genetic material at the locus and step an (B) includes the step of hybridizing a second oligonucleotide probe to the genetic material at the locus, wherein the first oligonucleotide probe and the second oligonucleotide probe are specific for the first allele and the second allele, respectively, at the locus.

7. A method according to claim 1, wherein step (A) is performed before step (C).

8. A method according to claim 1, wherein step (C) is performed before step (A).

9. A method according to claim 1, wherein the first allele-specific quantitative signal and the second allele-specific quantitative signal are each an optical signal.

10. A method according to claim 1, wherein the set of input data of step (C) includes the first reaction value and the second reaction value.

11. A method for determining a genotype of a subject at a locus within genetic material obtained from a biological sample from said subject, the method comprising:
- (A) reacting the material from said biological sample at the locus to produce a first reaction value indicative of the presence of a first allele at the locus within said genetic material, wherein the first reaction value is a measure of the intensity of a first allele-specific quantitative signal;
- (B) reacting the material from said biological sample at the locus to produce a second reaction value indicative of the presence of a second allele at the locus within said genetic material, wherein the second reaction value is a measure of the intensity of a second allele-specific quantitative signal;
- (C) accessing a set of input data, wherein said set of input data is comprised of pairs of data that are obtained under conditions that are comparable to the conditions under which said first reaction value and said second reaction value are obtained;
- (D) accessing an initial set of probability distributions, wherein said initial set of probability distributions comprises at least one probability distribution that associates a pair of hypothetical reaction values comprised of a first hypothetical reaction value and a second hypothetical reaction value with a corresponding probability for a genotype of interest at the locus;
- (E) applying the input data of step (C) to said initial set of probability distributions of step (D) to obtain a set of initial conditional probabilities of genotypes given the set of input data of (C);
- (F) forming a second set of probability distributions by applying data comprising the set of input data of step (C) and the initial conditional probabilities of genotypes of step (E), wherein said second set of probability distributions comprises at least one probability distribution that associates hypothetical pairs of reaction values with corresponding probabilities for a genotype of interest at the locus; and
- (G) applying said first reaction value and said second reaction value to the second set of probability distributions of step (F) to determine a measure of a conditional probability of each genotype of interest at the locus, wherein the conditional probability is a measure of the likelihood of the genotype of interest of the subject at the locus given the first reaction value and the second reaction value; and
- (H) determining the genotype of said subject at the locus based on the measure of conditional probability of step (G) of each genotype of interest at the locus for said subject, wherein each allele is a single specific nucleotide.

12. A method according to claim 11, wherein said second set of probability distributions is calculated to maximize the total likelihood of genotypes given the set of input data.

13. A method according to claim 11, wherein each pair of data in the set of input data of step (C) is expressed as a single numerical value.

14. A method according to claim 13, wherein the single numerical value is a ratio of the first reaction value and the second reaction value.

15. A method according to claim 11, wherein step (H) further includes a step of calculating a confidence score associated with the determination of the genotype in step (H), based on the measure of conditional probability from step (G).

16. A method according to claim 11, wherein step (F) further includes a step of calculating assumed genotypes for the set of input data of step (C) based on the initial conditional probabilities of genotypes of step (E), wherein the second set of probability distributions is formed by applying data comprising the set of input data of step (C) and the assumed genotypes for the set of input data.

17. A method according to claim 11, wherein the set of input data of step (C) includes the first reaction value and the second reaction value.

18. A method according to claim 11, wherein the first allele-specific quantitative signal and the second allele-specific quantitative signal are each an optical signal.

19. A method for determining a genotype of a subject at a locus comprising the method of claim 11, wherein step (A) is performed before step (C).

20. A method for determining a genotype of a subject at a locus comprising the method of claim 11, wherein step (C) is performed before step (A).

21. A method for determining a genotype of a subject at a locus within genetic material obtained from a biological sample from said subject, the method comprising:
- (A) reacting the material from said biological sample at the locus to produce a first reaction value indicative of the presence of a first allele at the locus within said genetic material, wherein the first reaction value is a measure of the intensity of a first allele-specific quantitative signal;
- (B) reacting the material from said biological sample at the locus to produce a second reaction value indicative of the presence of a second allele at the locus within said genetic material, wherein the second reaction value is a measure of the intensity of a second allele-specific quantitative signal;
- (C) accessing a set of input data, wherein said set of input data is comprised of pairs of data that are obtained under conditions that are comparable to the conditions under which said first reaction value and said second reaction value are obtained;
- (D) making a genotype guess for pairs of data in the set of input data;
- (E) calculating a set of probability distributions from the pairs of data in the set of input data and from the genotype guesses associated with the pairs of data, wherein said set of probability distributions comprises at least one probability distribution that associates a hypothetical first reaction value and a hypothetical second reaction value with a corresponding probability for a genotype of interest at the locus;
- (F) applying said first reaction value and said second reaction value to each probability distribution of interest of step (E) to determine a measure of a conditional probability of each genotype of interest at the locus, wherein the conditional probability is a measure of the likelihood of the genotype of interest of the subject at the locus given the first reaction value and the second reaction value; and
- (G) determining the genotype of the subject at the locus based on the measure of conditional probability of step (F), wherein each allele is a single specific nucleotide.

22. A method according to claim 21, wherein the set of input data includes the first reaction value and the second reaction value.

23. A method according to claim 21, further comprising a step of modifying the set of probability distributions of step (E) to find the maximally likely set of Genotype assignments given the set of input data.

24. A method according to claim 21, wherein the genotype guess of step (D) is made from a heuristic algorithm.

25. A method according to claim 21, wherein the pairs of data of step (D) are a subset of the set of input data.

26. A method for determining a genotype of a subject comprising the method of claim 21, wherein step (A) is performed before step (C).

27. A method for determining a genotype of a subject comprising the method of claim 21, wherein step (C) is performed before step (A).

* * * * *